US005776124A

United States Patent [19]

Wald

[11] Patent Number: 5,776,124

[45] Date of Patent: Jul. 7, 1998

[54] REUSABLE ADAPTER FOR UNITING A SYRINGE AND VIAL

[76] Inventor: Arnold Wald, 4019 West Victory Blvd., Burbank, Calif. 91505

[21] Appl. No.: 679,970

[22] Filed: Jul. 15, 1996

[51] Int. Cl.$^{6}$ .................. A61B 19/00

[52] U.S. Cl. .................. 604/403

[58] Field of Search .................. 604/403–407

[56] References Cited

U.S. PATENT DOCUMENTS

| | | | |
|---|---|---|---|
| 5,356,406 | 10/1994 | Schraga | 604/403 |
| 5,364,387 | 11/1994 | Sweeney | 604/403 |
| 5,374,264 | 12/1994 | Wadsworth, jr. | 604/403 |
| 5,472,022 | 12/1995 | Michel et al. | 604/403 |
| 5,533,994 | 7/1996 | Meyer | 604/403 |
| 5,569,236 | 10/1996 | Kriesel | 604/403 |

*Primary Examiner*—John G. Weiss
*Assistant Examiner*—Ki Yong O
*Attorney, Agent, or Firm*—William H. Maxwell

[57] ABSTRACT

A releasable adapter for coupling a hypodermic syringe and a medicinal vial having a pocket underlying a seal and separate from the chamber of the vial, characterized by a releasable primary attachment connected to and centering the adapter positioned on the vial, and a secondary attachment connected to and centering the syringe with the vial before the syringe needle pierces the seal and with limited projection of the syringe needle into said pocket, for withdrawing liquid when inverted as a unit.

14 Claims, 2 Drawing Sheets

REUSABLE ADAPTER FOR UNITING A SYRINGE AND VIAL

BACKGROUND OF THE INVENTION

This invention relates to the administration of medicinal liquids by means of a hypodermic syringe, whereby said liquid is withdrawn from a sealed vial and measured by volume for injection into the vascular system of a person. The pharmaceutical devices and proceedures are well established and standardized, in the involvement of both the vials for supplying medicinal liquids, and of the hypodermic syringes for measuring out the liquid withdrawn from the vials and for sterile injections thereof.

Heretofore, the two aforesaid articles, the vial and syringe, have been manipulated individually rather than as a unit, the typical injection process being a two-handed awkward operation for the person administering his or her own injection which is most often the case. For example, a first step involves one hand to hold the vial while the other hand forces the syringe needle to pierce the seal of the vial, there being no provision on either the vial or syringe to limit the depth of needle penetration. A second step involves one hand to hold both the vial and the syringe joined by the fragile needle, and the other hand to withdraw the syringe plunger a measured distance. This second step is manually perfomed with the needle of the syringe projecting approximately 0.500 inch (less the seal thickness) into the liquid content of the vial.

Firstly, the vial may or may not be completely filled and its volume content unknown. Secondly, the seal membrane of the vial is thin, for example 0.100 inch thick, which renders withdrawal of the needle to an optimum position a practical impossibility. The standard needle projection is approximately 0.500 inch, but no part of the vial or syringe is available to gage its penetration and/or withdrawal. As a result, the needle can be accidentally or unwittingly projected and air can be drawn into the syringe, and the needle can be damaged or bent and contaminated, due to the awkward conditions. Accordingly, it is a general object of this invention to provide an adapter for unitizing the vial and syringe combination, with minimal penetration of the needle, and all of which eliminates the awkward prior art conditions and ensures positive results.

It is an object of this invention to provide an adapter that fixedly couples a medicinal vial to a hypodermic syringe, coaxially and in determined longitudinal relationship. Joinder of the adapter to the vial and syringe respectively, can vary providing that they are held one to the other to withstand the forceful pressures of normal handling. In practice, the adapter is hooked onto the vial by releasable snap means, and the adapter grips the syringe by a releasable friction fit. The snap means and friction fit are disposed on a common longitudinal axis established in each of said members of the unitized combination, when assembled.

It is another object of this invention to provide an adapter that is positively attached and positioned on the vial to receive and guide the syringe and its penetrating needle, and such that the needle penetration is limited to a predetermined protrusion into a pocket within a plug that occupies the neck of the vial. In practice, the protruding end of the needle protrudes but does not enter into said vial chamber.

It is still another object of this invention to provide an adapter that guides the syringe needle concentrically on the common axis of these three aforementioned members, there being no propensity to damage or bend the needle.

Further, it is an object of this invention to provide a reusable adapter that can be repeatedly applied to and removed from successive expendable vials. In practice, the adapter as it is disclosed herein is made of a resilient material and is positively hooked onto the vial, and which can be twisted and thereby deformed for easy and quick removal for reuse.

Still further, it is an object of this invention to provide a monolithic adapter of integral body parts that can be injection molded of resilient plastic material, essentially without moving parts but rather deflectable parts, for effecting its assembly with and release from the vial. Also, assembly with and release from the syringe is by means of resilience, whereby the frictional tapered fit expands the adapter to securely grip and/or release the syringe.

SUMMARY OF THE INVENTION

A monolith of integral body parts is provided in an article formed as a adapter that couples a medicinal vial to a hypodermic syringe. The adapter is injection molded of a resilient plastic material that snaps onto the cap of the vial and which is subject to manual twisting to cause a misalignment that releases the adapter from the cap of the vial. The snap-on engagement of the adapter to the vial establishes a fixed relationship of the two members so that they become unitized. A feature of the adapter is its socket-like opening that centers and guides the hub of the syringe, so that the needle thereof is coaxial with the seal of the vial which it is to pierce for entry into a pocket within a plug that occupies the neck of the vial. Another feature of the adapter is its stop face that limits penetration of the needle through said seal, and ensures that it enters only into the pocket of the plug. By inverting the combined vial and syringe unit fixedly coupled by the adapter, substantially all of the liquid medication can be drawn from the vial by stopping withdrawal when liquid drops to the level of the being so that, there will be no withdrawal of air, and only a slight amount of liquid will remain in the pocket of the plug.

The foregoing and various other objects and features of this invention will be apparent and fully understood from the following detailed description of the typical preferred forms and applications thereof, throughout which description reference is made to the accompanying drawings.

THE DRAWINGS

Figures 1, 2, 3:
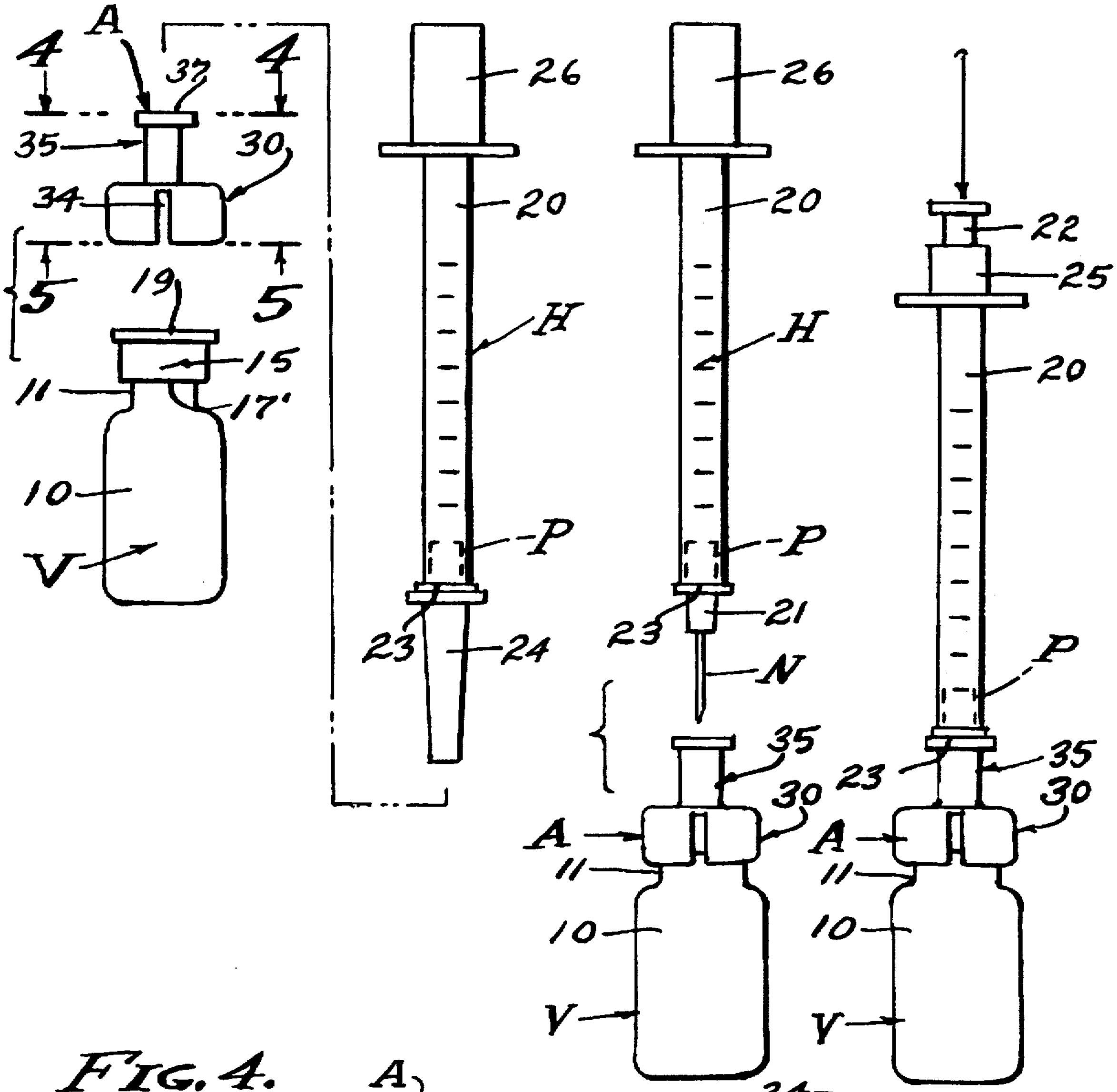
FIG. 1 is an exploded side view of the vial and the syringe with the adapter therebetween.
FIG. 2 is a view similar to FIG. 1, showing the adapter fixed to the vial, and showing the protector sleeve removed from the hub of the syringe so as to expose the needle.
FIG. 3 is a view similar to FIGS. 1 and 2, showing the syringe affixed to the adapter, and showing the protective cover removed from the operative plunger of the syringe.
Figure 4:
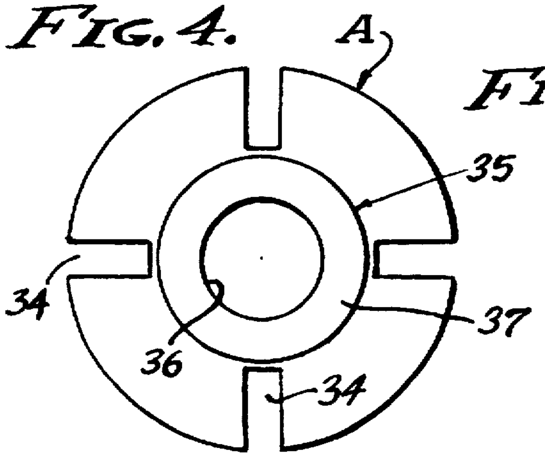
Figure 5:
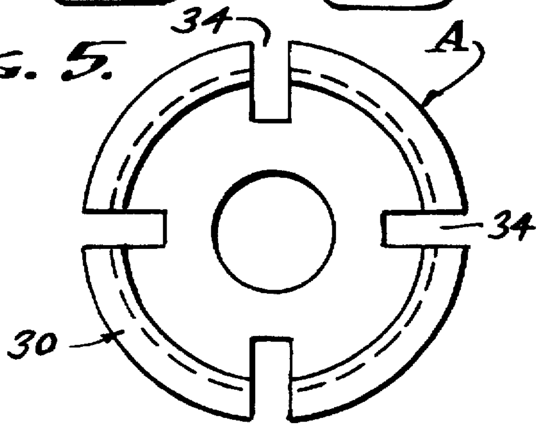

FIGS. 4 and 5 are opposite end views of the adapter, taken as indicated by lines 4—4 and 5—5 on FIG. 1.

Figure 6:
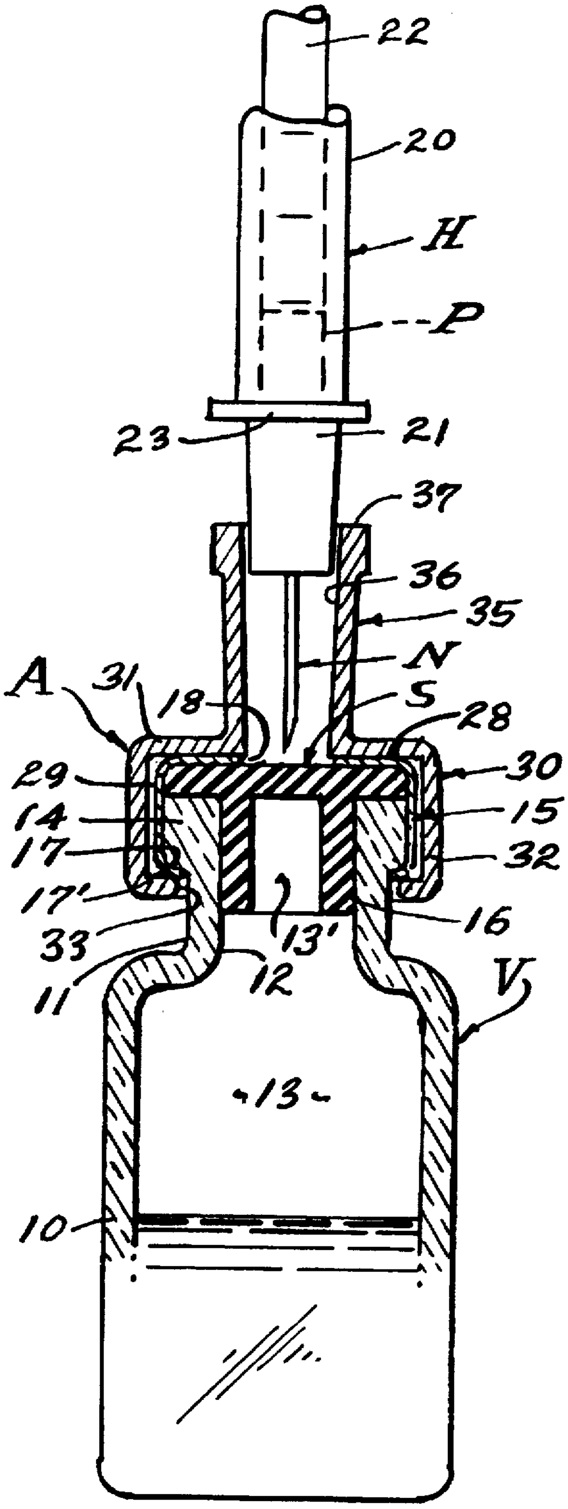

FIG. 6 is an enlarged detailed sectional view showing the alignment of the syringe needle with the seal of the vial, preparatory to piercing the seal.

Figure 7:
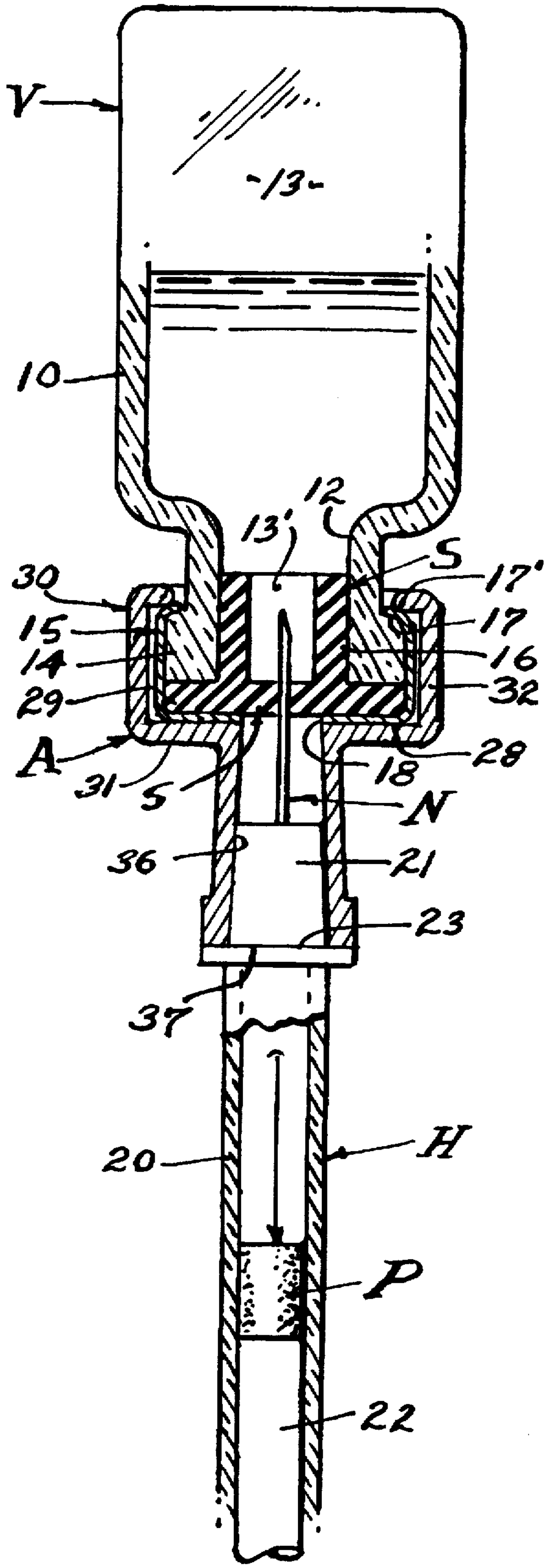

And FIG. 7 is an enlarged detailed sectional view showing the completed rigid assembly of the vial and the syringe coupled by the adapter, the assembly being inverted for use in withdrawing liquid from the vial.

PREFERRED EMBODIMENT

Referring now to the drawings, FIG. 1 illustrates the three separate articles involved, a vial V, a hypodermic syringe H, and the adapter A of this invention. The vial V and hypodermic syringe H are off-the-shelf commercial items that are employed herein as such, without any change or alteration. The adapter A is a utilitarian article that functions as a coupling cooperating with dissimilar features of the vial V and of the hypodermic syringe H, and protectively guides the hypodermic needle N.

The vial V is shown as a sterile 0.7 mL container in the form of a bottle or jar-like vessel 10 of transparent material closed by the seal S. The vessel has a neck 11 of reduced diameter and through which there is a cylindrical opening 12 into the liquid storage chamber 13 of the vessel. The top open end of the vial is characterized by a surrounding collar 14 of slightly larger diameter than the neck 11, forming a downwardly faced shoulder 17 for securement of a cap 15 that retains a plug that carries the seal S and closes the vessel chamber 13. The plug is comprised of a cylindrical core 16 that is pressed into the neck opening 12, and the overlying disc-shaped seal S is integral therewith. The disc-shaped seal S is a piercable elastomer approximately 0.100 inch thick with its bottom side coplanar with the top terminal end of the vial V.

Accordingly, the core 16 of the plug is tubular forming a small cylindrical pocket 13 (0.200 inch dia.) of limited depth underlying the seal and that opens into the pocket 13'. The cap 15 closely embraces the disc-shaped seal S and underlying collar 14 to permanently capture the seal and plug. In practice, the cap is made of maleable material such as soft aluminum 0.010 inch thick, that is rolled or swedged to engage beneath the shoulder 17. The Cap 15 is provided with an opening 18 (0.200 inch dia.) that exposes the center portion of the disc-shaped seal S, to be pierced by the hypodermic needle N for withdrawal of liquid from within the pocket 13' and from the vessel. As shown in FIG. 1 there is a removable protective shield 19 that ensures sterility of the seal S. Note that said shield 19 is removed before affixing the adapter A to the vial V as shown in FIG. 2.

The hypodermic syringe H is a sterile cylinder and piston device adapted to withdraw medicinal liquid from the vial V via a hypodermic needle N which is then employed to administer vascular injections. The syringe H has an elongated cylinder 20 of transparent material, closed at one end by a projecting elongated cylindrical hub 21 that carries the tubular needle N open into the cylinder, to transfer liquid and to receive the operating plunger 22 to which an elastomer piston P is attached. In practice for example and as shown, the hub 21 is slightly tapered (included angle 4°) and projects 0.250 inch from a stop flange 23. A removable protection sleeve 24 is carried by the hub and removed to expose the needle N (see FIG. 2). The other open end of the cylinder 20 is provided with a tubular enlargement 25 that carries a removable cover 26 that protectively encloses the extensible and retractile plunger 22 (see FIG. 7).

In accordance with this invention, the adapter A is provided to rigidly attach the hypodermic syringe H to the vial V, with the needle N positioned to withdraw liquid from said vial. A most common and standardized projection of the needle N from the hub 21 is 0.500 inch, it being an object of this invention to pierce the seal S to a midpoint of said needle (as shown in FIG. 7). The coupling features of the above described vial V and syringe H differ considerably in size and configuration, a primary fixed attachment means to the vial V and which involves the larger diameter affixing to the smooth surfaced cylindrical cap 15, and a secondary fixed attachment means to the hypodermic syringe H and which involves the smaller diameter affixing to the flanged hub 21. A feature of this invention is the positive coupled positioning of the syringe H with respect to the seal S of the vial V. Another feature is the releasable nature of said coupled positioning.

Referring now to the adapter A and its primary attachment means to the vial V, the cap 15 presents a flat top surface 28 normal to the center axis of the vial, an outer cylindrical wall 29 concentric with and surrounding said axis, and a downwardly faced shoulder 17' established by the rolled edge of the cap over the shoulder 17 of the vial. The vial V is known to have dimensional stability, and accordingly, the adapter A has a downwardly open cylindrical socket 30 with a top 31 that engages flat upon the surface 28, and a side wall 32 that slidably embraces the cylindrical surface 29. A feature is the inwardly turned detent 33 at the bottom edge of the socket, for locked engagement beneath the shoulder 17'. Thus, both radial and axial positioning is attained.

Engagement and disengagement of the detent 33 is by means of resilient deflection of the side wall 32, which permits temporary radial displacement of the detent 33 to slide over the cylindrical surface 29. In practice, the radial depth of the detent is about the same as or a little more than the 0.010 inch thickness of the cap 15 material. And in accordance with this invention, the socket 30 is of collet-like shape or configuration which is slotted at 34 to provide a plurality of circumferentially spaced spring legs and in the form of an interrupted wall 32.

The above described collet-like socket 30 configuration is not only conducive to the injection molding process of manufacture, but permits assembly and disassembly of the adapter A and vial V. That is, the axes of the adapter and of the vial can be manipulated out of alignment so as to spread the wall 32 and/or legs thereof for release. This principle is used to release the part from the mold core (not shown) and to assemble and disassemble the parts A and V.

Referring now to the adapter A and its secondary attachment means to the hypodermic syringe H, the tapered hub 21 and the stop shoulder 23 present small diameter features to center and guide the needle N. The syringe is known to have dimensional stability, and accordingly, the adapter A has an upwardly open tubular sleeve 35 integral with the socket 30 and open from the plane of the top 31 at the surface 28 and projecting upwardly to form an upwardly open tapered bore 36 to receive the hub 21 of the syringe H. The upper terminal end of the tubular sleeve 35 presents a flat stop surface 37 to engage the stop flange 23 and to thereby limit protrusion of the needle N into the pocket 13' so as to position the needle as shown in FIG. 7. A feature is entry of the tapered hub 21 (included angle 4°) into the guiding bore 36 so as to center the needle N before the needle N pierces the seal S (see FIG. 6). Another feature is the positioning of the end of the needle N within the pocket 13' so as to be submerged when the vial-adapter-syringe unit is inverted as shown in FIG. 7. And, when the stop flange 23 engages the stop surface 37 the tapered hub 21 is tightly gripped in the tapered socket (see FIG. 7). The assembly of vial V and syringe H is rigid and concentric with the axis of the adapter, as shown and hereinabove described.

Misalignment of adapter A axis from the vial V axis is facilitated by providing clearance between the outer diameter 29 of the cap 15 and the inner diameter of the surrounding wall 32, when installed. This enables a rocking movement of the adapter, whereby the detent 33 at one side forms a fulcrum about which the adapter tilts and is deflected to lift the diametrically opposite side of the detent 33 which then climbs over the rounded edge of the shoulder 17'. In practice, the detent 33 is radiused as shown, as are the top and bottom corner edges of the cap 15.

Having described only the preferred forms and applications of my invention, I do not wish to be limited or restricted to the specific details herein set forth, but wish to reserve to myself any modifications or variations that may appear to those skilled in the art as set forth within the limits of the following claims.

I claim:

1. An adapter for releasably connecting a medical syringe and a medicinal vial as a unit, the syringe being a cylinder and piston device for withdrawing and injecting liquid and having an elongated cylindrical hub carrying a tubular needle open into the cylinder for transferring said liquid and the needle projecting axially a determined distance from a flange, the vial being a vessel having a chamber for containing said liquid to be withdrawn therefrom and having a neck with an open top and a surrounding collar and an opening into the chamber of the vial and the open top being closed by a plug carrying a piercable seal and the plug having a pocket underlying the seal and open into the chamber of the vial, the adapter including;

a primary attachment means for releasable connection to the vial and comprised of a downwardly open cylindrical socket slidably engageable over the collar of the vial for fixed connection thereto, and a secondary attachment means for releasable connection to the syringe and comprised of an upwardly open tubular sleeve slidably receiving the cylindrical hub of the syringe for fixed connection thereto and for limited projection of the syringe needle to a position within the said plug pocket, the needle being submerged in the pocket below a low level of liquid in the vial when the vial-adapter-syringe as a unit is inverted.

2. The adapter for releasably connecting a medical syringe and a medicinal vial as a unit set forth in claim 1, wherein the downwardly open cylindrical socket of the primary attachment means has a top engageable with the open top of the vial for positioning the adapter on the vial.

3. The adapter for releasably connecting a medical syringe and a medicinal vial as a unit set forth in claim 1, wherein the downwardly open cylindrical socket of the primary attachment means has a flexible side wall with an inwardly turned detent releasably engageable with a shoulder formed by the collar of the vial.

4. The adapter for releasably connecting a medical syringe and a medicinal vial as a unit set forth in claim 1, wherein the downwardly open cylindrical socket of the primary attachment means has a flexible side wall slotted to form spring legs having inwardly turned detents releasably engageable with a shoulder formed by the collar of the vial.

5. The adapter for releasably connecting a medical syringe and a medicinal vial as a unit set forth in claim 3, the shoulder of the vial being downwardly faced from the bottom of the collar, and wherein the inwardly turned detent is upwardly faced and releasably engages with said downwarly faced shoulder of the vial.

6. The adapter for releasably connecting a medical syringe and a medicinal vial as a unit set forth in claim 4, the shoulder of the vial being downwardly faced from the bottom of the collar, whereby the spring legs having the inwardly turned upwardly faced detents releasably engage with said shoulder of the vial.

7. The adapter for releasably connecting a medical syringe and a medicinal vial as a unit set forth in claim 3, wherein the downwardly open socket of the primary attachment means has top engageable with the open top of the vial for positioning the adapter on the vial, and whereby the inwardly turned detent releasably engages with said shoulder of the vial.

8. The adapter for releasably connecting a medical syringe and a medicinal vial as a unit set forth in claim 1, wherein the downwardly open cylindrical socket of the primary attachment means has a top engageable with the open top of the vial for limiting projection of the tubular needle of the syringe through the seal and into the plug pocket.

9. The adapter for releasably connecting a medical syringe and a medicinal vial as a unit set forth in claim 1, wherein the upwardly open tubular sleeve of the secondary attachment means has stop surface engageable with the flange of the syringe and limiting projection of the needle of the syringe through the seal and into the plug pocket.

10. The adapter for releasably connecting a medical syringe and a medicinal vial as a unit set forth in claim 1, the hub of the syringe being tapered downwardly from the flange of the syringe, and wherein the upwardly open tubular sleeve of the secondary attachment means has a tapered bore releasably gripping the tapered hub of the syringe.

11. The adapter for releasably connecting a medical syringe and a medicinal vial as a unit set forth in claim 1, the hub of the syringe being tapered downwardly from a flange of the syringe, wherein the upwardly open tubular sleeve of the secondary attachment means has a tapered bore releasably gripping the tapered hub of the syringe, and wherein the upwardly open tubular sleeve of the secondary attachment means has a stop surface engageable with the flange of the syringe thereby limiting projection of the needle of the syringe through the seal and into the plug pocket.

12. The adapter for releasably connecting a medical syringe and a medicinal vial as a unit set forth in claim 1, wherein the downwardly open cylindrical socket of the primary attachment means has a top engageable with the open top of the vial and positioning the secondary attachment means on the vial, and wherein the upwardly open tubular sleeve of the secondary attachment means has a stop surface engageable with the flange of the syringe thereby limiting projection of the needle of the syringe through the seal and into the plug pocket.

13. The adapter for releasably connecting a medical syringe and a medicinal vial as a unit set forth in claim 3, wherein the downwardly open cylindrical socket of the primary attachment means has a flexible side wall with an inwardly turned detent releasably engageable with said shoulder of the vial, the hub of the syringe being tapered downwardly from the flange of the syringe, and wherein the upwardly open tubular sleeve of the secondary attachment means has a tapered bore releasably gripping the tapered hub of the syringe.

14. The adapter for releasably connecting a medical syringe and a medicinal vial as a unit set forth in claim 3, wherein the downwardly open cylindrical socket of the primary attachment means has a flexible side wall slotted to form spring legs having inwardly turned detents releasably engageable with said shoulder, the hub of the syringe being tapered downwardly from the flange of the syringe, wherein the upwardly open tubular sleeve of the secondary attachment means has a tapered bore releasably gripping the tapered hub of the syringe, and wherein the upwardly open tubular sleeve of the secondary attachment means has a top surface engageable with the flange of the syringe and limiting projection of the needle of the syringe through the seal and into the plug pocket.

* * * * *